(12) United States Patent
Engman et al.

(10) Patent No.: US 11,819,704 B2
(45) Date of Patent: Nov. 21, 2023

(54) POSITIVE SYSTEM ALERTS

(71) Applicant: West Affum Holdings Corp., Grand Cayman (KY)

(72) Inventors: Zoie R. Engman, Kirkland, WA (US); Pamela F. Breske, Newcastle, WA (US); Erick M. Roane, Bellevue, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 276 days.

(21) Appl. No.: 17/173,975

(22) Filed: Feb. 11, 2021

(65) Prior Publication Data

US 2022/0054849 A1 Feb. 24, 2022

Related U.S. Application Data

(60) Provisional application No. 63/068,772, filed on Aug. 21, 2020.

(51) Int. Cl.
*A61N 1/39* (2006.01)
*A61N 1/04* (2006.01)

(52) U.S. Cl.
CPC ........... *A61N 1/3904* (2017.08); *A61N 1/046* (2013.01); *A61N 1/0484* (2013.01); *A61N 1/3925* (2013.01); *A61N 1/3968* (2013.01); *A61N 1/3993* (2013.01); *A61N 1/39622* (2017.08)

(58) Field of Classification Search
CPC ................ A61N 1/3904; A61N 1/3925; A61N 1/3968
See application file for complete search history.

(56) References Cited

U.S. PATENT DOCUMENTS

| 3,724,355 A | 4/1973 | Unger |
| 4,583,524 A | 4/1986 | Hutchins |
| 4,619,265 A | 10/1986 | Morgan et al. |
| 4,928,690 A | 5/1990 | Heilman et al. |

(Continued)

FOREIGN PATENT DOCUMENTS

WO 1998039061 A2 9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Eric D. Bertram
(74) *Attorney, Agent, or Firm* — Columbia IP Law

(57) ABSTRACT

In one embodiment, a method to alert a user of a wearable cardioverter defibrillator (WCD) is described. The method includes determining when a system issue is resolved and issuing an alert when the system issue is resolved. In some embodiments, the method may detect the system issue and issuing a system alert based at least in part on the system issue. The method may then monitor a status of the system issue. In some instances, the method may detect an abnormality in system operation sand determine a severity rating for the abnormality. The method may determine if the abnormality satisfies a time duration threshold based at least in part on the severity rating.

19 Claims, 10 Drawing Sheets

(56) References Cited

U.S. PATENT DOCUMENTS

| | | |
|---|---|---|
| 4,955,381 A | 9/1990 | Way et al. |
| 5,078,134 A | 1/1992 | Heilman et al. |
| 5,228,449 A | 7/1993 | Christ et al. |
| 5,285,792 A * | 2/1994 | Sjoquist ............... A61N 1/3925 600/510 |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 10/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 11,334,826 B2 * | 5/2022 | Engman ............... A61N 1/3904 |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |
| 2016/0328529 A1 * | 11/2016 | Kaib ...................... G16H 40/40 |

OTHER PUBLICATIONS

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

* cited by examiner

POSITIVE SYSTEM ALERTS

CROSS REFERENCE TO RELATED PATENT APPLICATIONS

This patent application claims benefit of U.S. Provisional Patent Application No. 63/068,772 filed Aug. 21, 2020 and is incorporated herein by reference in their entirety for all purposes.

BACKGROUND

When people suffer from some types of heart arrhythmias, in some instances, blood flow to various parts of the body may be reduced. Some arrhythmias can result in a Sudden Cardiac Arrest (SCA). SCA can lead to death very quickly, e.g., within 10 minutes, unless treated in the interim. Some observers have thought that SCA is the same as a heart attack, which it is not.

Some people have an increased risk of SCA. Such people may include patients who have had a heart attack or a prior SCA episode. A frequent recommendation for these people is to receive an Implantable Cardioverter Defibrillator (ICD). The ICD is surgically implanted in the chest, and continuously monitors the patient's intracardiac electrogram (IEGM). If certain types of heart arrhythmias are detected, then the ICD delivers an electric shock through the heart.

As a further precaution, people who have been identified to have an increased risk of a SCA are sometimes given a Wearable Cardioverter Defibrillator (WCD) system to wear until an ICD is implanted. Early versions of such systems were called wearable cardiac defibrillator systems. A WCD system typically includes a harness, vest, belt, or other garment that the patient wears. The WCD system further includes electronic components, such as a defibrillator and electrodes, coupled to the harness, vest, or another garment. When the patient wears the WCD system, the electrodes may electrically contact the patient's skin, and aid in sensing the patient's electrocardiogram (ECG). If a shockable heart arrhythmia (e.g., ventricular fibrillation or VF) is detected from the ECG, then the defibrillator delivers an appropriate electric shock through the patient's body, and thus through the heart. The delivered shock may restart the patient's heart and save the patient's life.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes instances and examples of cardiac monitoring systems (e.g., WCD systems), devices, systems, storage media that may store programs, and methods.

In one embodiment, a method to alert a user of a WCD is described. The method includes determining when a system issue is resolved and issuing an alert when the system issue is resolved.

In some embodiments, the method may detect the system issue and issue a system alert based at least in part on the system issue. The method may then monitor a status of the system issue. In some instances, the method may detect an abnormality in system operations and determine a severity rating for the abnormality. The method may determine if the abnormality satisfies a time duration threshold based at least in part on the severity rating.

In some embodiments, the alert may include one of emitting a tone, changing display content, illuminating at least one LED, emitting a vibration pattern, and some combination thereof. In some instances, the user may customize the alert. In some embodiments, the alert may introduce one alert mode at a time. In some embodiments, the method may activate a voice alert after a predetermined time threshold has been satisfied. In some embodiments, the alert may be issued for a predetermined time frame.

In further embodiments, the method may enter a discrete user interface mode when the predetermined time frame has been satisfied. The discrete user interface mode may include setting a display screen to standby mode. The method may include deactivating the alert based at least in part on user input.

In another embodiment, a wearable cardiac defibrillator (WCD) system for monitoring health of a patient wearing the WCD system is described. The system includes a support structure configured to be worn by a patient and an electronics module configured to be coupled to the support structure. One or more processors are in communication with the electronic module. The one or more processors configured to cause the system to determine when a system issue is resolved and issue an alert when the system issue is resolved.

In some embodiments, the system issue may be detected, and a system alert may be issued based at least in part on the system issue. A status of the system issue may be monitored. An abnormality in system operations may be detected and a severity rating for the abnormality may be determined. In some embodiments, the processor may determine if the abnormality exceeds a time duration threshold based at least in part on the severity rating.

In some instances, the alert may include one of emitting a tone, changing display content, illuminating at least one LED, emitting a vibration pattern, and some combination thereof. The user may customize the alert. The alert may be introduced one alert mode at a time. The processor may activate a voice alert after a predetermined time threshold has been satisfied. In some embodiments, the alert may be issued for a predetermined time frame. The processor may enter a discrete user interface mode when the predetermined time frame has been satisfied. In some embodiments, the discrete user interface mode may include setting a display screen to standby mode. In some instances, the processor may deactivate the alert based at least in part on user input.

In another embodiment, a method to alert a user of a wearable cardioverter defibrillator (WCD) is described. The method includes detecting a system issue and issuing a system alert based at least in part on the system issue. The method includes monitoring a status of the system issue and determining when the system issue is resolved. The method also includes issuing an alert when the system issue is resolved and deactivating the alert based at least in part on user input.

In one embodiment, a WCD system for monitoring health of a patient wearing the WCD system is described. The system includes a support structure configured to be worn by a patient and an electronics module configured to be coupled to the support structure. One or more LEDs are in communication with the electronics module, the one or more LEDs positioned on an outside of the electronics module.

In some embodiments, the system also includes one or more processors in communication with the electronic module. The processor may change the luminous intensity of the one or more LEDs. In some embodiments, the processor may illuminate the one or more LEDs based on one or more of a system status, a patient status, an electronics module status, or some combination thereof.

In some embodiments, the processor may change a pattern of illumination of the one or more LEDs. In one embodiment, the processor may deactivate at least of the one or more LEDs after a predetermined threshold has been satisfied. In one embodiment, the processor may alter a color of the one or more LEDs. In some embodiments, the one or more LEDs may include at least two LEDs and the processor may illuminate the two or more LEDs in a sequential, syncing pattern.

In some embodiments, the one or more LEDs may include at least two LEDs and the processor may alter a color of the at least two LEDs. The at least one LED may be a first color and the at least a second LED may be a second color.

In one embodiment, a method to alert a user of a WCD is described. The method includes illuminating one or more LEDs proximate the WCD based on one or more of a system status, a patient status, an electronics module status, or some combination thereof.

In another embodiment, the method may include altering a pattern of illumination of the one or more LEDs. The method may include deactivating at least of the one or more LEDs after a predetermined threshold has been satisfied. In some embodiments, the method may include altering a color of the one or more LEDs. In one embodiment, the method may include illuminating at least two LEDs in a sequential, syncing pattern. In some embodiments, the method may include altering a color of the at least two LEDs, wherein at least one LED is a first color and at least a second LED is a second color.

In a further embodiment, a WCD system for monitoring health of a patient wearing the WCD system is described. The system includes a support structure configured to be worn by a patient and an electronics module configured to be coupled to the support structure. One or more LEDs are coupled to the electronics module. The one or more LEDs are positioned on an outside of the electronics module. One or more processors are in communication with the electronic module. The one or more processors configured to cause the system to detect a system status, a patient status, an electronics module status, or some combination thereof, illuminate the one or more LEDs based on one or more of based at least in part on the detection, and deactivate at least of the one or more LEDs after a predetermined threshold has been satisfied.

In an embodiment, a wearable cardiac defibrillator (WCD) system for monitoring health of a patient wearing the WCD system. The system includes a support structure configured to be worn by a patient and an electronics module configured to be coupled to the support structure. The system includes one or more displays proximate the electronics module and one or more processors in communication with the electronic module. The one or more processors configured to cause the system to activate the one or more displays and adjust a brightness of the one or more displays based at least in part on an illumination threshold.

In some embodiments, the illumination threshold may include an operational status, a patient status, a system status, an environmental status, an alarm status, and some combination thereof. In some embodiments, the one or more displays may be a passive, reflective LCD display. In some embodiments, the processor may detect a system irregularity with the WCD and increase the brightness of the one or more displays based at least in part on the system irregularity. In some embodiments, the processor may detect a patient physiological condition, increase the brightness of the one or more displays based at least in part on the patient physiological condition.

In some embodiments, the processor may detect a brightness of ambient lighting proximate the WCD and increase the brightness of the one or more displays based at least in part on the brightness of the ambient lighting. In some embodiments, the processor may detect a user input to the WCD and increase the brightness of the one or more displays based at least in part on the user input. In some instances, the processor may detect a time of day and increase the brightness of the one or more displays based at least in part on the time of day. In some instances, the processor may detect an orientation of the electronics module and increase the brightness of the one or more displays based at least in part on the orientation of the electronics module.

In some instances, the processor may determine a length of time the brightness has been activated and decrease the brightness of the one or more displays when a time threshold has been satisfied. In some embodiments, the time threshold may be between 1 minute and 5 minutes. In some instances, the processor may determine a force acting on the WCD and increase the brightness of the one or more displays when the force has satisfied a force threshold. In some instances, the processor may detect an audible input proximate the WCD and increase the brightness of the one or more displays when the audible input matches a wake term. In some instances, a mobile device may be in communication with the processor and the processor may increase a brightness of the one or more displays when a command is received from the mobile device.

In one embodiment, a method to manipulate one or more displays of a WCD is described. The method includes activating the one or more displays and adjusting a brightness of the one or more displays based at least in part on an illumination threshold.

In some instances, the illumination threshold may include an operational status, a patient status, a system status, an environmental status, an alarm status, and some combination thereof. In some instances, the one or more displays may be a passive, reflective LCD display. In some instances, the method may include detecting a system irregularity with the WCD and increasing the brightness of the one or more displays based at least in part on the system irregularity. In some instances, the method may include detecting a patient physiological condition and increasing the brightness of the one or more displays based at least in part on the patient physiological condition.

In some instances, the method may include detecting a brightness of ambient lighting proximate the WCD and increasing the brightness of the one or more displays based at least in part on the brightness of the ambient lighting. In some instances, the method may include detecting a user input to the WCD and increasing the brightness of the one or more displays based at least in part on the user input.

In some instances, the method may include detecting a time of day and increasing the brightness of the one or more displays based at least in part on the time of day. In some instances, the method may include detecting an orientation of the electronics module and increasing the brightness of the one or more displays based at least in part on the orientation of the electronics module. In some instances, the method may include determining a length of time the brightness has been activated and decreasing the brightness of the one or more displays when a time threshold has been satisfied. The time threshold may be between 1 minute and 5 minutes.

In some embodiments, the method may include determining a force acting on the WCD and increasing the brightness of the one or more displays when the force has satisfied a force threshold. In some embodiments, the method may include detecting an audible input proximate the WCD and increasing the brightness of the one or more displays when the audible input matches a wake term. The method may include increasing a brightness of the one or more displays when a command is received from a mobile device.

In another embodiment, a WCD system for monitoring health of a patient wearing the WCD system is described. The system includes a support structure configured to be worn by a patient and an electronics module configured to be coupled to the support structure. The system also includes one or more displays proximate the electronics module and one or more processors in communication with the electronic module. The one or more displays are a passive, reflective LCD displays. The one or more processors are configured to cause the system to adjust a brightness of the one or more displays based at least in part on an illumination threshold, wherein the illumination threshold includes an operational status, a patient status, a system status, an environmental status, an alarm status, and some combination thereof

BRIEF DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
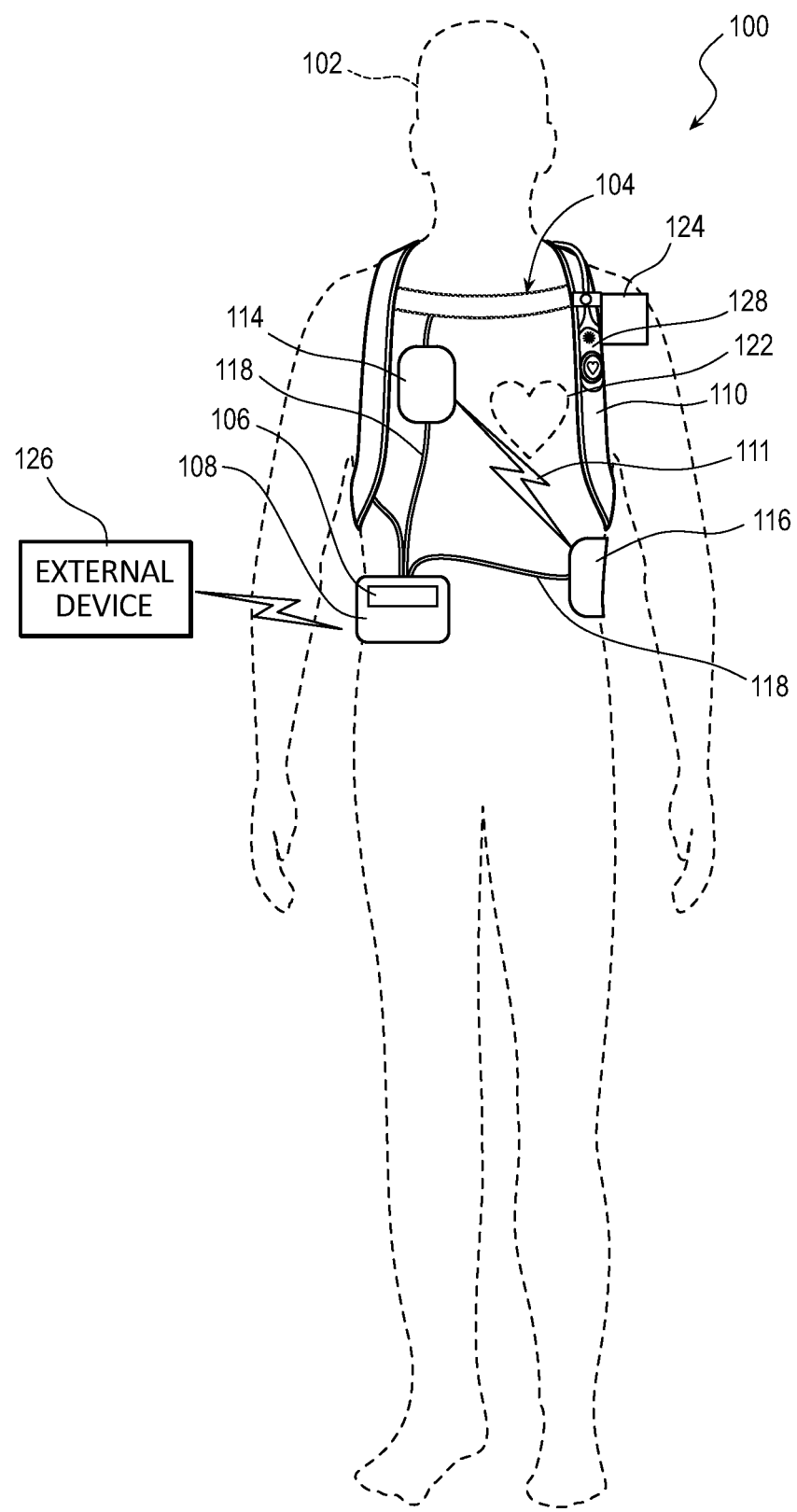
FIG. 1 is a diagram of a sample WCD system in accordance with exemplary embodiments described herein.

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCDs) are worn by patients at risk for sudden cardiac arrest. WCDs have one or more haptic responses to provide user feedback. The display may include visual responses such as LEDs and a user interface design (UI design), audible responses, and the like. However, in some situations, the display may provide excessive feedback in terms of light, noise, and the like. As described below, in some embodiments, the WCD display may optimize feedback to a user while remaining discrete and unassuming. Some ways to optimize user feedback via the WCD display include LED intensity behavior, display blacklight behavior, providing positive feedback, and the like.

For example, in some embodiments, some WCDs may include one or more LEDs. The one or more LEDs may provide visual feedback to a user. The LEDs may be used as operational status indicators to convey the current state of the device. For example, LEDs can be easily manipulated. LEDs can be turned on and off, the intensity can be adjusted, the illumination pattern can vary, the color can vary, and, if more than one LED is present, a combination of these changes can be combined.

The ability to easily manipulate LEDs allows the WCD to communicate various WCD statuses to a user. For example, the WCD can use the various LEDs to communicate a system state of the WCD, ambient light detection, user input, time of day, orientation, duration of time, force exerted on the WCD, sound, and other behaviors.

In another embodiment, the WCD may provide positive feedback to the user using the WCD interface. The display may be used to present operational status indicators, like icons that depict the current state of the device. The display may be passive, reflective, LCD that allows visual content to be continuously provided, and if needed, the display can be illuminated to increase visibility of the screen content in certain conditions. The positive feedback may assure the user that the WCD is operating properly or that an issue has been resolved. In some embodiments, the feedback may increase a user's confidence in the system behavior by actively informing the user when an issue is resolved and the WCD is operational.

FIG. 1 illustrates a system 100 with a patient 102 wearing an example of a WCD system 104 according to embodiments described herein. In some embodiments, the WCD system 104 may include one or more communication devices 106, a support structure 110, and an external defibrillator 108 connected to two or more defibrillation electrodes 114, 116, among other components.

The support structure 110 may be worn by the patient 102. The patient 102 may be ambulatory, meaning the patient 102 can walk around and is not necessarily bed-ridden while wearing the wearable portion of the WCD system 104. While the patient 102 may be considered a "user" of the WCD system 104, this is not a requirement. For instance, a user of the WCD system 104 may also be a clinician such as a doctor, nurse, emergency medical technician (EMT) or other similarly tasked individual or group of individuals. In some cases, a user may even be a bystander. The particular context of these and other related terms within this description should be interpreted accordingly.

In some embodiments, the support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso 112 of the patient 102. A second component may rest more towards a patient's hips, whereby the second component may be positioned such that the patient's hips support the heavier components of the WCD system 104. In some embodiments, the heavier components of the WCD system 104 may be carried via a shoulder strap or may be kept close to the patient 102 such as in a cart, bag, stroller, wheelchair, or other vehicle.

The external defibrillator 108 may be coupled to the support structure 110 or may be carried remotely from the patient 102. The external defibrillator 108 may be triggered to deliver an electric shock to the patient 102 when patient 102 wears the WCD system 104. For example, if certain thresholds are exceeded or met, the external defibrillator 108 may engage and deliver a shock to the patient 102.

The defibrillation electrodes 114, 116 can be configured to be worn by patient 102 in a number of ways. For instance, the defibrillator 108 and the defibrillation electrodes 114, 116 can be coupled to the support structure 110 directly or indirectly. For example, the support structure 110 can be configured to be worn by the patient 102 to maintain at least one of the electrodes 114, 116 on the body of the patient 102, while the patient 102 is moving around, etc. The electrodes 114, 116 can be thus maintained on the torso 112 by being attached to the skin of patient 102, simply pressed against the skin directly or through garments, etc. In some embodiments, the electrodes 114, 116 are not necessarily pressed against the skin but becomes biased that way upon sensing a condition that could merit intervention by the WCD system 104. In addition, many of the components of defibrillator 108 can be considered coupled to support structure 110 directly, or indirectly via at least one of defibrillation electrodes 114, 116.

The WCD system 104 may defibrillate the patient 102 by delivering an electrical charge, pulse, or shock 111 to the patient 102 through a series of electrodes 114, 116 positioned on the torso 112. For example, when defibrillation electrodes 114, 116 are in good electrical contact with the torso 112 of patient 102, the defibrillator 108 can administer, via electrodes 114, 116, a brief, strong electric pulse 111 through the body. The pulse 111 is also known as shock, defibrillation shock, therapy, electrotherapy, therapy shock, etc. The pulse 111 is intended to go through and restart heart 122, in an effort to save the life of patient 102. The pulse 111 can further include one or more pacing pulses of lesser magnitude to pace heart 122 if needed. The electrodes 114, 116 may be electrically coupled to the external defibrillator 108 via a series of electrode leads 118. The defibrillator 108 may administer an electric shock 111 to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116.

In some embodiments, the WCD system 104 may also include either an external or internal monitoring device or some combination thereof. FIG. 1 displays an external monitoring device 124 which may also be known as an outside monitoring device. The monitoring device 124 may monitor at least one local parameter. Local parameters may include a physical state of the patient 102 such as ECG, movement, heartrate, pulse, temperature, and the like. Local parameters may also include a parameter of the WCD 104, environmental parameters, or the like. For example, in some embodiments, the monitoring device 124 may include sensors to gather patient movement, ambient lighting, and the like. The monitoring device 124 may be physically coupled to the support structure 110 or may be proximate the support structure 110. In either location, the monitoring device 124 is communicatively coupled with other components of the WCD 104.

For some of these parameters, the device 124 may include one or more sensors or transducers. Each one of such sensors can be configured to sense a parameter of the patient 102, and to render an input responsive to the sensed parameter. In some embodiments, the input is quantitative, such as values of a sensed parameter; in other embodiments, the input is qualitative, such as informing whether or not a threshold is crossed. In some instances, these inputs about the patient 102 are also referred to herein as patient physiological inputs and patient inputs. In some embodiments, a sensor can be construed more broadly, as encompassing many individual sensors.

In some embodiments, a communication device 106 may enable the patient 102 to interact with, and garnish data from, the WCD system 104. The communication device 106 may enable a patient or third party to view patient data, dismiss a shock if the patient is still conscious, turn off an alarm, and otherwise engage with the WCD system 104. In some instances, the communication device 106 may transfer or transmit information include patient data to a third-party data server such as a cloud server or a blockchain server. In some embodiments, the communication device 106 may be a separable part of an external defibrillator 108. For example, the communication device 106 may be a separate device coupled to the external defibrillator 108. In some embodiments, the communication device 106 may be wired or wirelessly linked to the external defibrillator 108 and may be removable from the defibrillator 108. In other embodiments, the communication device 106 may form an inseparable assembly and share internal components with the external defibrillator 108. In some embodiments, the WCD system 104 may include more than one communication device 106. For example, the defibrillator 108 may include components able to communicate to the patient and the WCD system 104 may include a separate communication device 106 remote form the defibrillator 108.

In some embodiments, the communication device 106 may be communicatively coupled to an alert button 128. The alert button 128 may be removably coupled to the support structure 110. The patient 102 may couple the alert button 128 to the support structure 110 or may couple the alert button 128 to an article of clothing. The alert button 128 may have a wired connection or be wirelessly connected to the communication device 106. In some embodiments, the alert button 128 may include a visual output, an audio output, and a user input. The visual output may include a light, such as an LED, a small screen, or some combination thereof. Likewise, the audio output may include one or more speakers. The output of the audio output may be loud enough to be heard over nominal background noise. In some embodiments, the audio output might have an adjustable volume range. In some embodiments, the alert button 128 may include a microphone. In still further embodiments, the alert button 128 may also include a haptic response.

In some embodiments, the defibrillator 108 may connect with one or more external devices 126. For example, as shown in FIG. 1, the defibrillator 108 may connect to various external devices 126 such as the cloud, a remote desktop, a laptop, a mobile device, or other external device using a network such as the Internet, local area networks, wide area networks, virtual private networks (VPN), other communication networks or channels, or any combination thereof.

In embodiments, one or more of the components of the exemplary WCD system 104 may be customized for the patient 102. Customization may include a number of aspects including, but not limited to, fitting the support structure 110 to the torso 112 of patient 102; baseline physiological parameters of patient 102 can be measured, such as the heart rate of patient 102 while resting, while walking, motion detector outputs while walking, etc. The measured values of such baseline physiological parameters can be used to customize the WCD system, in order to make its analysis more accurate, since patients' bodies differ from one another. Of course, such parameter values can be stored in a memory of the WCD system, and the like. Moreover, a programming interface can be made according to embodiments, which receives such measured values of baseline physiological parameters. Such a programming interface may input automatically in the WCD system these, along with other data.

Figure 2:
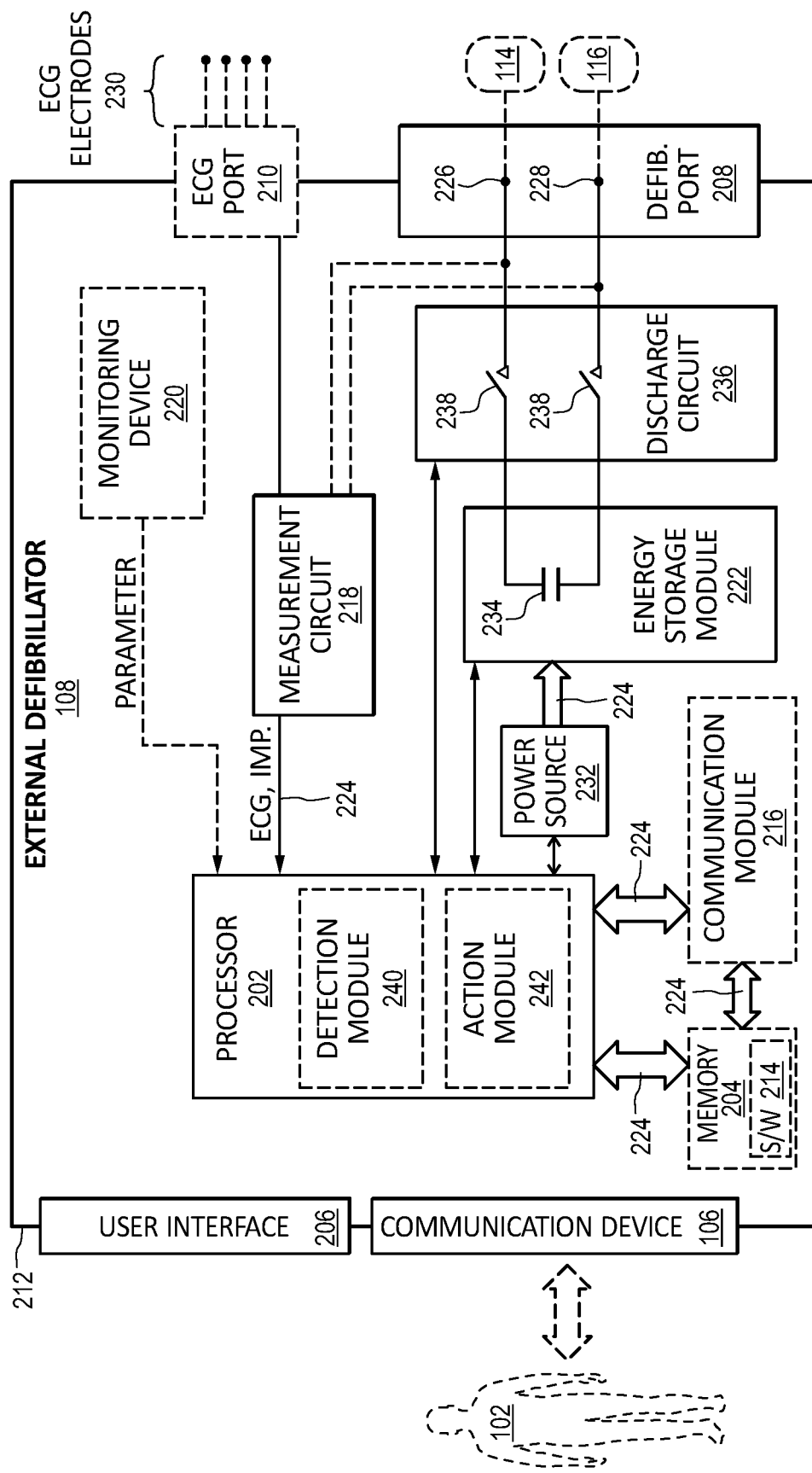
FIG. 2 is a block diagram of an example defibrillator in accordance with exemplary embodiments described herein.

FIG. 2 is a diagram displaying various components of an example external defibrillator 108. The external defibrillator 108 may be an example of the defibrillator 108 described with reference to FIG. 1. The components shown in FIG. 2 may be contained within a single unit or may be separated amongst two or more units in communication with each other. The defibrillator 108 may include a communication device 106, processor 202, memory 204, defibrillation port 208, and ECG port 210, among other components. In some embodiments, the components are contained within a housing 212 or casing. The housing 212 may comprise a hard shell around the components or may comprise a softer shell for increased patient comfort.

The communication device 106, processor 202, memory 204 (including software/firmware code (SW) 214), defibrillation port 208, ECG port 210, communication module 216, measurement circuit 218, monitoring device 220, and energy storage module 222 may communicate, directly or indirectly, with one another via one or more buses 224. The one or more buses 224 may allow data communication between the elements and/or modules of the defibrillator 108.

The memory 204 may include random access memory (RAM), read only memory (ROM), flash RAM, and/or other types. The memory 204 may store computer-readable, computer-executable software/firmware code 214 including instructions that, when executed, cause the processor 202 to perform various functions (e.g., determine shock criteria, determine heart rate, issue shock command, issue alerts, etc.). In some embodiments, the processor 202 may include an intelligent hardware device, e.g., a central processing unit (CPU), a microcontroller, an application-specific integrated circuit (ASIC), etc.

In some embodiments, the memory 204 can contain, among other things, the Basic Input-Output system (BIOS) which may control basic hardware and/or software operations such interactions and workings of the various components of the defibrillator 108, and in some embodiments, components external to the defibrillator 108. For example, the memory 204 may contain various modules to implement the workings of the defibrillator 108 and other aspects of the present disclosure.

In some embodiments, the defibrillator 108 may include a user interface 206. The user interface 406 may be in addition to or part of the communication device 106. The user interface 406 may display an ECG of the patient, a status of the defibrillator 108, a status of a charge (e.g., a battery charge or an energy storage module), and the like.

In some embodiments, the defibrillator 108 may include a defibrillation port 208. The defibrillation port 208 may comprise a socket, opening, or electrical connection in the housing 212. In some instances, the defibrillation port 208 may include two or more nodes 226, 228. The two or more nodes 226, 228 may accept two or more defibrillation electrodes (e.g., defibrillation electrodes 114, 116, FIG. 1). The nodes 226, 228 may provide an electrical connection between the defibrillation electrodes 114, 116 and the defibrillator 108. The defibrillation electrodes 114, 116 may plug into the two or more nodes 226, 228 via one or more leads (e.g., leads 118), or, in some instances, the defibrillation electrodes 114, 116 may be hardwired to the nodes 226, 228. Once an electrical connection is established between the defibrillation port 208 and the electrodes 114, 116, the defibrillator 108 may be able to deliver an electric shock to the patient 102.

In some embodiments, the defibrillator 108 may include an ECG port 210 in the housing 212. The ECG port 210 may accept one or more ECG electrodes 230 or ECG leads. In some instances, the ECG electrodes 230 sense a patient's ECG signal. For example, the ECG electrodes 230 may record electrical activity generated by heart muscle depolarization, timing, or both. The ECG electrodes 230 may utilize 4-leads to 12-leads or multichannel ECG, or the like. The ECG electrodes 230 may connect with the patient's skin.

In some embodiments, the defibrillator 108 may include a measurement circuit 218. The measurement circuit 218 may be in communication with the ECG port 210. For example, the measurement circuit 218 may receive physiological signals from ECG port 210. The measurement circuit 218 may additionally or alternatively receive physiological signals via the defibrillation port 208 when defibrillation electrodes 114, 116 are attached to the patient 102. The measurement circuit 218 may determine a patient's ECG signal from a difference in voltage between the defibrillation electrodes 114, 116.

In some embodiments, the measurement circuit 218 may monitor the electrical connection between the defibrillation electrodes 114, 116 and the skin of the patient 102. For example, the measurement circuit 218 can detect impedance between electrodes 114, 116. The impedance may indicate the effective resistance of an electric circuit. An impedance calculation may determine when the electrodes 114, 116 have a good electrical connection with the patient's body.

In some embodiments, the defibrillator 108 may include an internal monitoring device 220 within the housing 212. The monitoring device 220 may monitor at least one local parameter. Local parameters may include physical state of the patient such as ECG, movement, heartrate, pulse, temperature, and the like. Local parameters may also include a parameter of the WCD system (e.g., WCD 104, FIG. 1), defibrillator 108, environmental parameters, or the like.

In some embodiments, the WCD system 104 may include an internal monitoring device 220 and an external monitoring device (e.g., external monitoring device 124). If both monitoring devices 124, 220 are present, the monitoring devices 124, 220 may work together to parse out specific parameters depending on position, location, and other factors. For example, the external monitoring device 124 may monitor environmental parameters while the internal monitoring device 220 may monitor patient and system parameters.

In some embodiments, the defibrillator 108 may include a power source 232. The power source 232 may comprise a battery or battery pack, which may be rechargeable. In some instances, the power source 232 may comprise a series of different batteries to ensure the defibrillator 108 has power. For example, the power source 232 may include a series of rechargeable batteries as a prime power source and a series of non-rechargeable batteries as a secondary source. If the patient 102 is proximate an AC power source, such as when sitting down, sleeping, or the like, the power source 232 may include an AC override wherein the power source 232 draws power from the AC source.

In some embodiments, the defibrillator 108 may include an energy storage module 222. The energy storage module 222 may store electrical energy in preparation or anticipation of providing a sudden discharge of electrical energy to the patient. In some embodiments, the energy storage module 222 may have its own power source and/or battery pack. In other embodiments, the energy storage module 222 may pull power from the power source 232. In still further embodiments, the energy storage module 222 may include one or more capacitors 234. The one or more capacitors 234 may store an electrical charge, which may be administered to the patient. The processor 202 may be communicatively coupled to the energy storage module 222 to trigger the amount and timing of electrical energy to provide to the defibrillation port 208 and, subsequently, the patient 102.

In some embodiments, the defibrillator 108 may include a discharge circuit 236. The discharge circuit 236 may control the energy stored in the energy storage module 222. For example, the discharge circuit 236 may either electrical couple or decouple the energy storage module 222 to the defibrillation port 208. The discharge circuit 236 may be communicatively coupled to the processor 202 to control when the energy storage module 222 and the defibrillation port 208 should or should not be coupled to either administer or prevent a charge from emitting from the defibrillator 108. In some embodiments, the discharge circuit 236 may include on or more switches 238. In further embodiments, the one or more switches 238 may include an H-bridge.

In some embodiments, the defibrillator 108 may include a communication module 216. The communication module 216 may establish one or more communication links with either local hardware and/or software to the WCD system 104 and defibrillator 108 or to remote hardwire separate from the WCD system 104. In some embodiments, the communication module 216 may include one or more antennas, processors, and the like. The communication module 216 may communicate wirelessly via radio frequency, electromagnetics, local area networks (LAN), wide area networks (WAN), virtual private networks (VPN), RFID, Bluetooth, cellular networks, and the like. The communication module 216 may facilitate communication of data and commands such as patient data, episode information, therapy attempted, CPR performance, system data, environmental data, and so on. In some embodiments, the communication module 216 may include a display screen to display messages to the patient. In some embodiments, the display screen may be a touch screen, backlit screen, passive, reflective LCD screen or the like.

In further embodiments, the communication module 216 may include one or more LEDs which may also be used to convey information to the patient. In some embodiments, the LED brightness may be modulated, the LEDs may be color changing, and the like. In some embodiments, if multiple LEDs are present, each LED may represent various bits of information. For example, one LED may represent heartrate information and enable the patient to quickly determine their heart is operating normally. Another LED may represent the heartrate signal to ensure the patient the heartrate readings are being properly transmitted. Another LED may also represent system status and allow the patient to easily ascertain that the system is fully functioning.

In some embodiments, the processor 202 may execute one or more modules. For example, the processor 202 may execute a detection module 240 and/or an action module 242. The detection module 240 may be a logic device or algorithm to determine if any or a variety of thresholds are exceeded which may require action of the defibrillator 108. For example, the detection module 240 may receive and interpret all of the signals from the ECG port 210, the defibrillation port 208, the monitoring device 220, an external monitoring device, and the like. The detection module 240 may process the information to ensure the patient is still conscious and healthy. If any parameter indicates the patient 102 may be experiencing distress or indicating a cardiac episode, the detection module 240 may activate the action module 242.

The action module 242 may receive data from the detection module 240 and perform a series of actions. For example, an episode may merely be a loss of battery power at the power source 232 or the energy storage module 222, or one or more electrodes (e.g., ECG electrodes, defibrillation electrodes) may have lost connection. In such instances, the action module 242 may trigger an alert to the patient or to an outside source of the present situation. This may include activating an alert module. If an episode is a health risk, such as a cardiac event, the action module 242 may begin a series of steps. This may include issuing a warning to the patient, issuing a warning to a third party, priming the energy storage module 222 for defibrillation, releasing one or more conductive fluids proximate defibrillation electrodes 114, 116, and the like.

Figure 3:
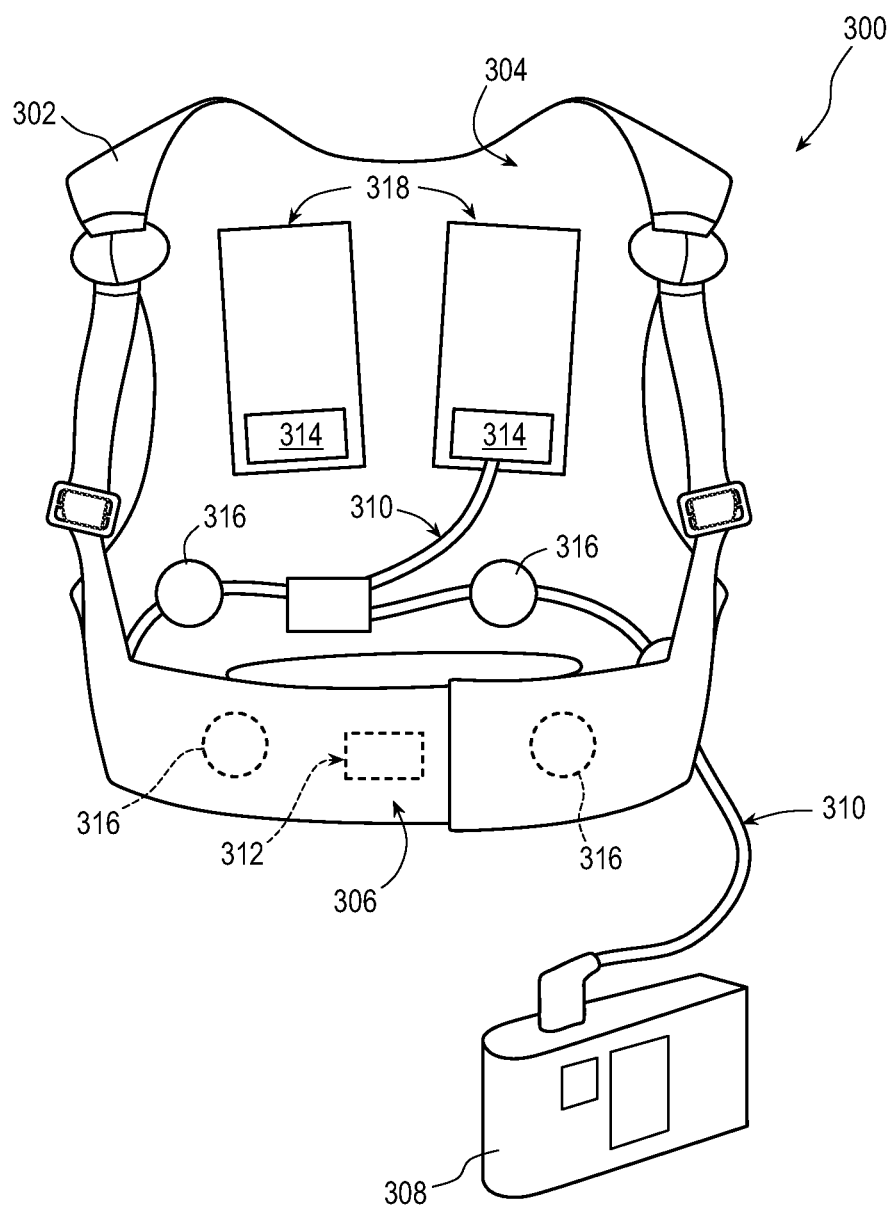
FIG. 3 is a diagram of sample embodiments of components of a WCD system in accordance with exemplary embodiments described herein.

FIG. 3 is a diagram of sample embodiments of components of a WCD system 300 according to exemplary embodiments. The WCD system 300 may be an example of the WCD system 104 describe with reference to FIG. 1. In some embodiments, the WCD system 300 may include a support structure 302 comprising a vest-like wearable garment. In some embodiments, the support structure 302 has a back side 304, and a front side 306 that closes in front of a chest of the patient.

In some embodiments, the WCD system 300 may also include an external defibrillator 308. The external defibrillator 308 may be an example of the defibrillator 108 describe with reference to FIGS. 1 and 2. As illustrated, FIG. 3 does not show any support for the external defibrillator 308, but as discussed, the defibrillator 308 may be carried in a purse, on a belt, by a strap over the shoulder, and the like as discussed previously. One or more wires 310 may connect the external defibrillator 308 to one or more electrodes 312, 314, 316. Of the connected electrodes, electrodes 312, 314 are defibrillation electrodes, and electrodes 316 are ECG sensing electrodes.

The support structure 302 is worn by the patient to maintain electrodes 312, 314, 316 on a body of the patient. For example, the back-defibrillation electrodes 314 are maintained in pockets 318. In some embodiments, the inside of the pockets 318 may comprise loose netting, so that the electrodes 314 can contact the back of the patient. In some instances, a conductive fluid may be deployed to increase connectivity. Additionally, in some embodiments, sensing electrodes 316 are maintained in positions that surround the patient's torso, for sensing ECG signals and/or the impedance of the patient.

In some instances, the ECG signals in a WCD system 300 may comprise too much electrical noise to be useful. To ameliorate the problem, multiple ECG sensing electrodes 316 are provided, for presenting many options to the processor (e.g., processor 202, FIG. 2). The multiple ECG sensing electrodes 316 provide different vectors for sensing the ECG signal of the patient.

Figure 4:
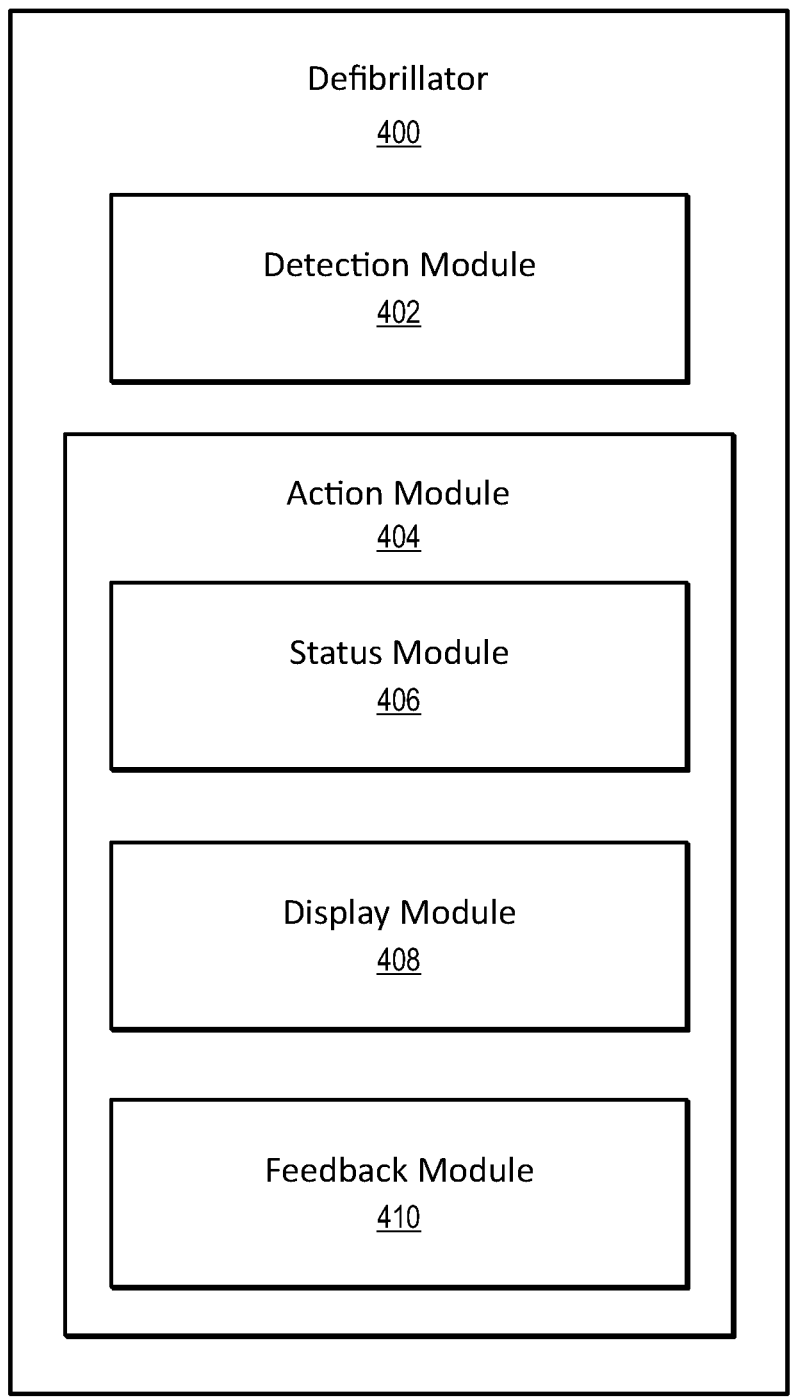
FIG. 4 is a block diagram of an example defibrillator in accordance with exemplary embodiments described herein.

FIG. 4 is a block diagram illustrating components of one example of a defibrillator 400. The defibrillator 400 may be an example of the defibrillator 108 described with reference to FIGS. 1 and 2 and defibrillator 308 described with reference to FIG. 3. In this example, the defibrillator 400 has a detection module 402 and an action module 404. The detection module 402 and action module 404 may be examples of the detection module 240 and action module 242 described with reference to FIG. 2. In some embodiments, the action module 404 may include a heart rate (HR) analysis module 406, a consistency module 408, and shock determination module 410.

The detection module 402 may aid in the detection of various shockable conditions. For example, the detection module 402 may receive a signal from at least one electrode and analyze the signal for a heart rate and other indicators of an abnormal heart condition. If a shockable or monitoring condition exists, the detection module 402 may communicate the need for action to the action module 404.

In some embodiments, the detection module 402 may also detect system conditions. For example, the detection module 402 may determine a battery status of the defibrillator. This may enable the detection module 402 to issue an alert when the battery status is below an acceptable threshold. The detection module 402 may also monitor a status of the electrodes to determine if the electrodes are properly secured to the patient and the leads are all functioning appropriately. The detection module 402 may also track a status of the various other components of the WCD system, such as the alert button, remote monitoring device, and the like. The detection module 402 may track conditions of the defibrillator itself. For example, the detection module 402 may detect device orientation, movement, external forces, and the like.

In some embodiments, the detection module 402 may also detect ambient and external conditions. For example, the detection module 402 may detect environmental conditions such as noise levels, lighting levels, weather conditions, and the like. The detection module 402 may monitor time of day, in some embodiments, the detection module 402 may monitor the patient's habits through the day and days of the week.

In some embodiments, based at least in part on information and data from the detection module 402, the action module 404 may take one or more actions. For example, in some embodiments, the action module 404 may have a status module 406, a display module 408, and a feedback module 410.

The status module 406 may control one or more LEDs proximate the defibrillator, alarm button, or some combination thereof. The status module 406 may illuminate the LEDs in a variety of ways to communicate various system alerts, status, or the like. For example, as shown in FIG. 5A-5D, the status module 406 may illuminate the one or more LEDs based on a variety of conditions such as patient health, system status, system alerts, and the like.

Figure 5A:
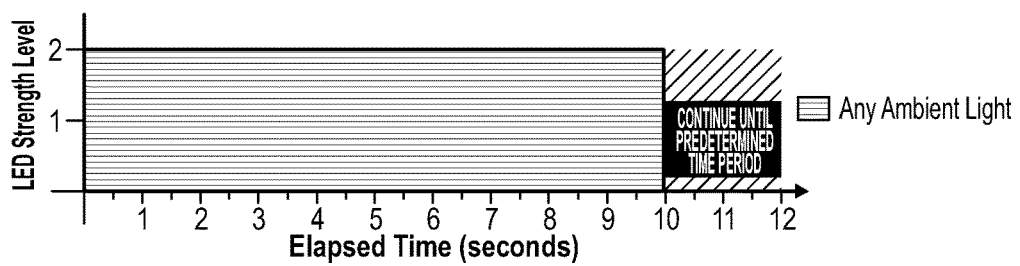
FIG. 5a through FIG. 5e are graphical representations of different LED illumination patterns according to exemplary embodiments described herein.

As seen in FIG. 5A, in some embodiments, the LED may illuminate at full strength for an indefinite amount of time. The status module 406 may illuminate one LED, or multiple LEDS. In some embodiments, the LEDs may maintain the same color. For example, the status module 406 may maintain a single LED at a first color for an undetermined period of time or until a condition threshold is satisfied. In another embodiments, the status module 406 may maintain a single LED at full strength but change the color between a first color and one or more second colors. In still a further embodiment, the status module 406 may illuminate multiple LEDs at a constant brightness and the same color or different colors for an undetermined period of time or until a condition threshold is satisfied.

Figure 5B:
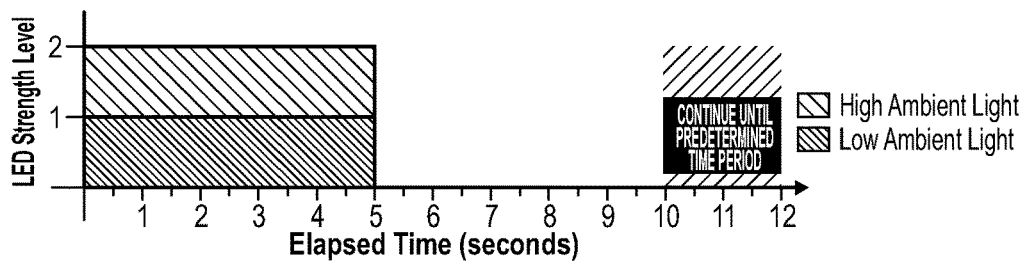

As seen in FIG. 5B, in some embodiments, the status module may adjust the LED strength based on the amount of ambient light. For example, in some embodiments, the LED may be communicating or indicating a non-essential alert or condition and adjusting the brightness of the LED(s) may present a less intrusive condition for the user. Again, the status module 406 may illuminate one or more LEDs a variety of colors for an undetermined period of time or until a condition threshold is satisfied.

Figure 5C:
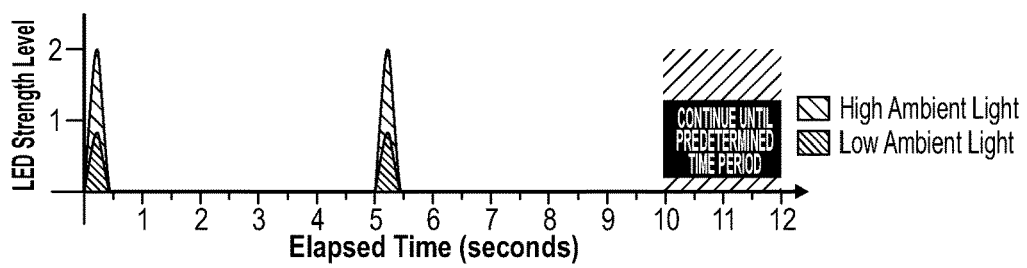

FIG. 5C illustrating a pulsing LED light. In some embodiments, the strength of the pulsing LED may vary based on the strength of ambient light. Again, the status module 406 may illuminate one LED or multiple LEDs. The status module 406 may vary the color of one or more LEDs. For example, in some embodiments, the color may be consistent. In other embodiments, the color of the LED may change between pulses. If multiple LEDs are present, the colors the various LEDs may represent various conditions that may be present. In some embodiments, the status module 406 may continuing pulsing the one or more LEDs until a condition threshold is satisfied.

Figure 5D:
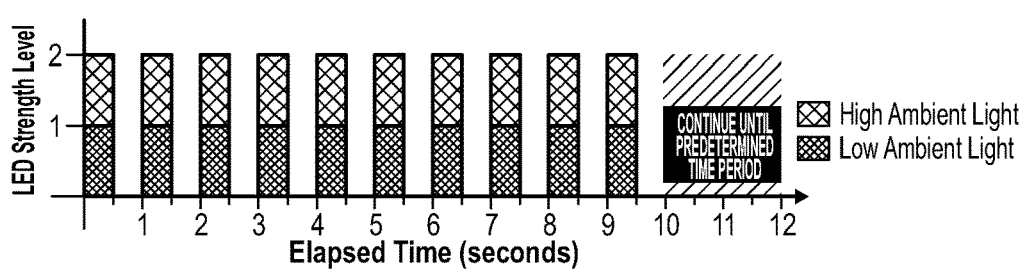

FIG. 5D represents a blinking LED with varying strength levels based on ambient light conditions. In some embodiments, the strength of the pulsing LED may vary based on the strength of ambient light. Again, the status module 406 may illuminate one LED or multiple LEDs. The status module 406 may vary the color of one or more LEDs. For example, in some embodiments, the color may be consistent. In other embodiments, the color of the LED may change between blinks. If multiple LEDs are present, the colors the various LEDs may represent various conditions that may be present. In some embodiments, the status module 406 may continuing blinking the one or more LEDs until a condition threshold is satisfied.

Figure 5E:
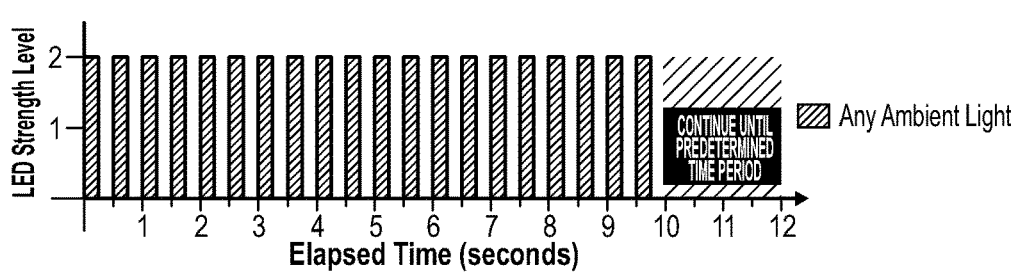

FIG. 5E represents a flashing LED with varying strength levels based on ambient light conditions. In some embodiments, the strength of the pulsing LED may vary based on the strength of ambient light. Again, the status module 406 may illuminate one LED or multiple LEDs. The status module 406 may vary the color of one or more LEDs. For example, in some embodiments, the color may be consistent. In other embodiments, the color of the LED may change between flashes. If multiple LEDs are present, the colors the various LEDs may represent various conditions that may be present. In some embodiments, the status module 406 may continuing flashing the one or more LEDs until a condition threshold is satisfied.

Referring back to FIG. 4, in some embodiments, a display module 408 may modulate a brightness of one or more displays proximate the defibrillator 400 based at least in part on ambient light conditions. In some embodiments, the display module 408 may vary the brightness between off or standby mode to 100% brightness. For example, in some embodiments, the defibrillator 400 may include an ambient light sensor and a visual display screen. The display may be used to present operational status indicators, for example, the screen may illuminate various icons, verbal warnings or alerts, and the like. In some embodiments, the display may be passive, reflective LCD which may enable visual content to be continuously provided. In some instances, the display may be illuminated to increase visibility of the screen content under predetermined conditions. The display module 408 may manipulate the backlight in a variety of conditions.

For example, in some embodiments, the display module 408 may modulate the screen brightness based on the amount of ambient lighting. To reduce brightness and distractions, the screen may dim when the amount of ambient lighting is low. Likewise, to increase visibility, the screen may brighten when the amount of ambient lighting is high. In still further embodiments, the display module 408 may put the display in a standby mode. The defibrillator 400 is still functioning and monitoring the patient but the display may be off to reduce any distractions, preserve battery life, and the like.

In some embodiments, the display module 408 may enter standby mode after a predetermined time of inactivity. Inactivity may be categorized as a lack of system alerts, health alerts, patient movement, ambient light, ambient sound, and the like or some combination thereof. For example, if a patient is sleeping, the display module 408 may determine a time of day combined with a lack of device movement and enter standby mode after a predetermined period of time.

In some embodiments, the display module 408 may manipulate the backlight based on a variety of system conditions. For example, in some embodiments, the display module 408 may toggle the backlight based at least in part on a system state. For example, if the system is running properly, the display may enter standby mode. However, if a system error or malfunction is detected, the display module 408 may illuminate the display. In another example, the display module 408 may modulate the display backlight based at least in part on a patient's physiological condition. For example, if an abnormality is detected, the display module 408 may illuminate the display.

In some embodiments, the display module 408 may also register user input. For example, the display module 408 may illuminate if activated by the user. The user activation may be a button proximate the defibrillator 400, or if the display is a touch screen, the display module 408 may register the user's touch. In some embodiments, the display module 408 may also activate the display based on movement of defibrillator 400. For example, if the user shakes, taps, or reorients the defibrillator, the display module 408 may activate the screen. In some embodiments, the defibrillator 400 may also register a fall and may activate the screen. The fall may register via an accelerometer proximate the defibrillator 400 which may sense a sudden fast movement. In some embodiments, if a fall is detected, the defibrillator may be programmed to alert emergency personnel.

In some embodiments, the display module 408 may activate based on audible inputs. For example, the defibrillator may have a microphone and the display module 408 may be programmed to activate based on key phrases. In some embodiments, the display module 408 may be pre-programmed with key phrases; in other embodiments, the user may pre-program the key phrases. For example, the display module 408 may activate the display when the user says "Hey WCD" or "Hey Defibrillator" or "Hey Defib" or some such phrase. The display module 408 may also be keyed to other phrases such as "What's my heart rate," "Is everything okay?" or the like.

In further embodiments, the display module 408 may activate or deactivate a display based on input from a remote device. For example, the display module 408 may activate based on input from the alert button (e.g., alert button 128, FIG. 1), an external device (e.g., external device 126, FIG. 1), a monitoring device (e.g., monitoring device 124, FIG. 1), a mobile device, or the like. In some embodiments, the remote device may communicatively couple to the display module 408. This may allow the remote device to activate the display or can toggle the display on and off. In another embodiment, the display module 408 may toggle the display on when a connection with a remote device is activated or during pairing operation or some combination thereof.

In some embodiments, the feedback module 410 may provide user feedback based on a variety of conditions. For example, the feedback module 410 may provide positive feedback to the user. In some embodiments, the positive feedback may assure the assure that the WCD system and the defibrillator 400 are operating properly. This may include offering positive feedback when an issue has been resolved. The feedback module 410 may increase a confidence of the user in system behavior by actively informing the user when an issue is resolved or when the system is properly operating. In some embodiments, the feedback module 410 may provide feedback by emitting a tone, emitting a vibration pattern, displaying content on the screen, using LEDs with specific patterns, or some combination thereof. The specific feedback mechanism may change based on the specific issue resolution, system status, or the like.

In one example, the feedback module 410 may simultaneously use an LED, backlight, vibration, and audible behavior to immediately inform the suer of a resolution of a specific issue. After the predetermined alert time, the feedback module 410 ceases all alert activity. For example, the feedback module 410 may issue a positive feedback alert for one second or as long as 20 seconds. In some embodiments, the alert may not be continuous but may flash, blink, or pulse for the predetermined time period.

In some embodiments, the feedback module 410 may enter a discrete feedback mode. During a discrete feedback mode, the LED, backlight, vibration, and audio may be in a standby mode until either user input is detected or the system status changes.

The feedback module 410 may allow a user to positively confirm that an issue was resolved rather than waiting to see if an alert continues. For example, if an electrode is not properly attached, the system may issue an alarm for a predetermined period of time. In some instances, the user may not properly correct the electrode issue but will only receive feedback when the electrode alert reissues. The feedback module 410 may enable the user to troubleshoot the electrode issue until a positive notification of issue resolution is received.

Figure 6:
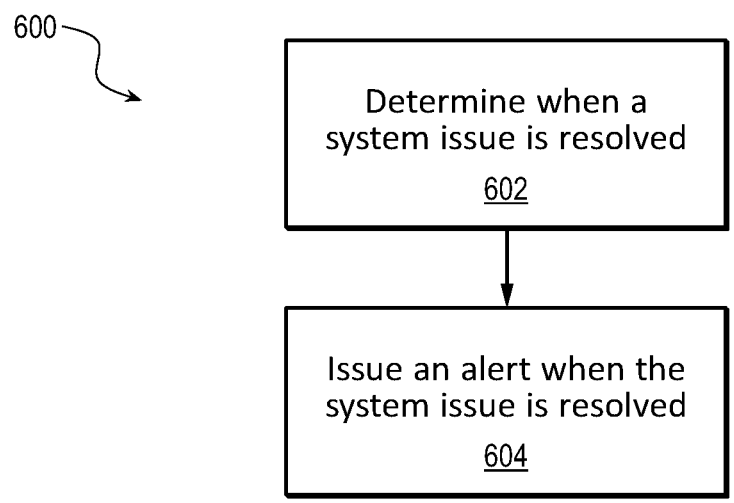
FIG. 6 is a flow diagram in accordance with exemplary embodiments described herein.

FIG. 6 is a flow chart illustrating an example of a method 600 for WCD systems, in accordance with various aspects of the present disclosure. For clarity, the method 600 is described below with reference to aspects of one or more of the systems described herein.

At block 602, the method 600 may determine when a system issue is resolved. For example, the system may have any number of issues that rewire a user or third party to correct. The method may track the various issues present in a WCD system to determine when the issue has been remedied.

At block 604, the method 600 may issue an alert when the system issue is resolved. For example, the method 600 emit a tone or audio, change display content, illuminate at least one LED, emit a vibration pattern, or some combination thereof to alert the user to the positive resolution of an issue. In some embodiments, the method 600 may have a sequence of alerts. For example, the LED may blink green, then the display may provide a positive resolution method. In other embodiments, the method 600 may simply emit a tone or jingle that notifies the user. In some instances, the user may customize the tone and/or jingle. In still further embodiments, the user may customize the positive alert. For example, one user might prefer a blinking LED while another user may prefer a happy jingle and a haptic response.

In some embodiments, the type of positive alert may also depend on the system issue. For example, if the user actively took steps to remedy a situation, the alert might be more substantial that a passive system fix issue. In some embodiments, the method 600 may activate a voice alert. The voice alert may be a standard voice alert or may be customized per the patient's preference.

In some embodiments, the alert may issue for a predetermined period of time. For example, rather than having an infinite alert, the alert may issue then quickly terminate. For example, the alert may be less than a second to a minute in length. The predetermined time period may be customized to the specific issue, the patient, or both. In some instances, an LED may only illuminate or blink for a quickly for less than a few seconds. In other embodiments, the haptic alert may vibrate for 10 seconds. After the predetermined time frame, the method 600 may deactivate a display proximate the defibrillator. For example, the method 600 may enter a discrete user interface mode wherein the display may no longer illuminate or distract the patient. This may set the display to enter a standby mode. In another embodiment, the alert may deactivate based on user input. The user may press a button proximate the defibrillator, tap or shake the defibrillator, or use a touch screen or the like.

Thus, the method 600 may provide for one method of providing positive feedback to a user of a WCD system. It should be noted that the method 600 is just one implementation and that the operations of the method 600 may be rearranged or otherwise modified such that other implementations are possible.

Figure 7:
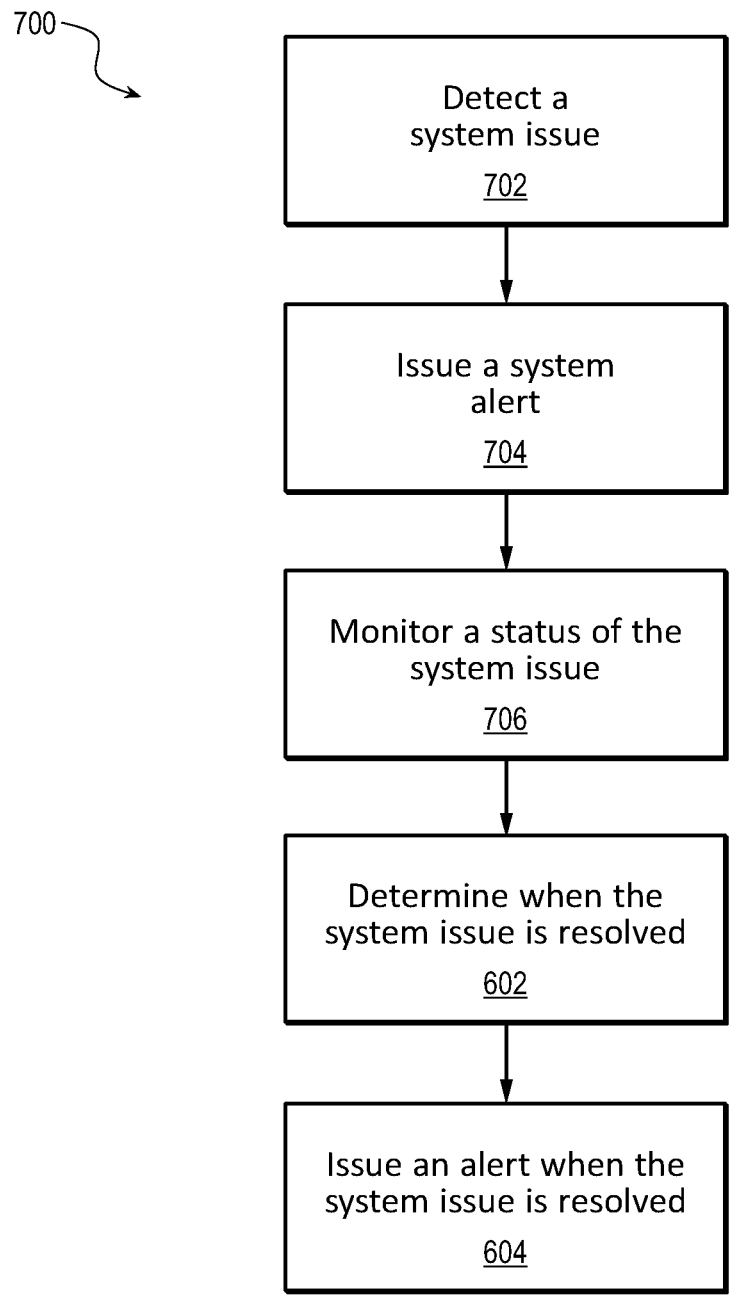
FIG. 7 is a flow diagram in accordance with exemplary embodiments described herein.

FIG. 7 is a flow chart illustrating an example of a method 700 for WCD systems, in accordance with various aspects of the present disclosure. For clarity, the method 700 is described below with reference to aspects of one or more of the systems described herein.

At block 702, the method 700 may detect a system issue. The system issue may be a battery issue, an ECG connectivity issue, an electrode connectivity issue, a lead being disengaged, a Wi-Fi connectivity issue, damage to the WCD system, or the like. Essentially a system issue may be anything that is not physiological involving patient health.

At block 704, the method 700 may issue a system alert. The system alert may be a notification to the patient of the issue and troubleshooting issues. After the alert has been issued, at block 706, the method 700 may monitor a status of the system issue. For example, the method 700 may continuously check to see if the issue has been resolved. At block 602, the method 700 may determine the issue is resolved and, at block 604, issue an alert. In some embodiments, Thus, the method 700 may provide for one method of providing positive feedback to a user of a WCD system. It should be noted that the method 700 is just one implementation and that the operations of the method 700 may be rearranged or otherwise modified such that other implementations are possible.

Figure 8:
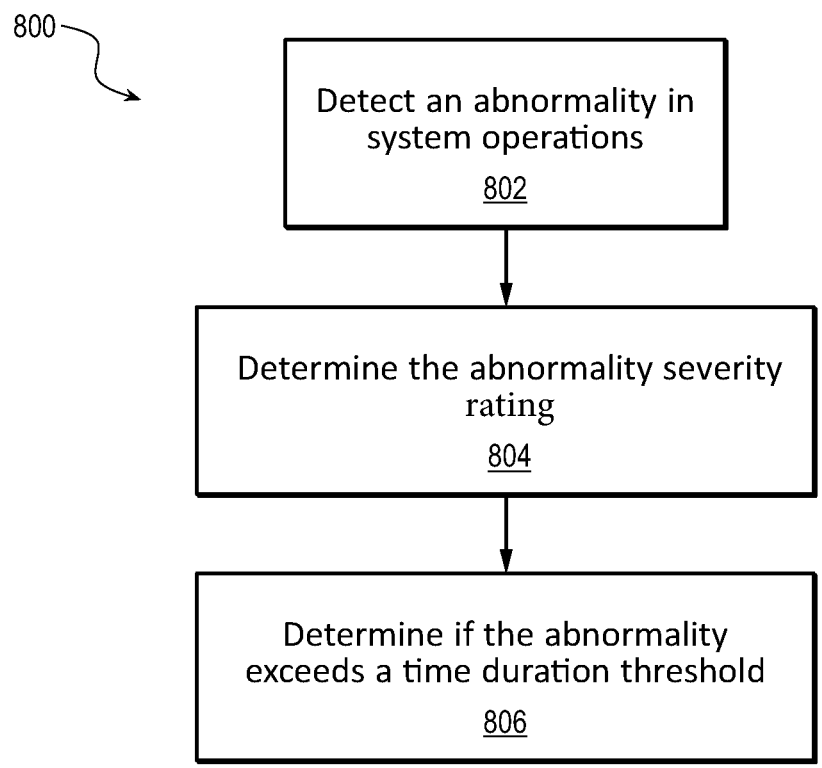
FIG. 8 is a flow diagram in accordance with exemplary embodiments described herein.

FIG. 8 is a flow chart illustrating an example of a method 800 for WCD systems, in accordance with various aspects of the present disclosure. For clarity, the method 800 is described below with reference to aspects of one or more of the systems described herein.

At block 802, the method 800 may detect an abnormality in system operations. For example, the method 800 may detect if the patient's heart rate data is not being detected or if there is too much noise in the signal from the sensors. The method 800 may categorize and quantify the system abnormality.

At block 804, the method may determine if the abnormality exceeds a predetermined severity threshold. For example, the method 800 may determine a severity threshold or a severity rating for the abnormality. The severity rating may provide an acceptable time duration for the abnormality. For example, a more severe abnormality such an improper, low quality, or lack of heart rate readings is more severe and has a lower time threshold due to healthy concerns. However, a low battery charge may be sustainable for a longer period of time. Likewise, a lost connection with a remote device may be more sustainable for a longer period of time.

At block 806, the method 800 may determine if the abnormality exceeds the appropriate time duration threshold. If the abnormality has continued, the method 800 may emit another alert warning the patient that the current troubleshooting is not resolving the problem. This may also provide the patient with the affirmative feedback that their efforts are not successful, and they need to keep troubleshooting the issue until they receive the positive resolution alert.

Thus, the method 800 may provide for one method of providing positive feedback to a user of a WCD system. It should be noted that the method 800 is just one implementation and that the operations of the method 800 may be rearranged or otherwise modified such that other implementations are possible.

Figure 9:
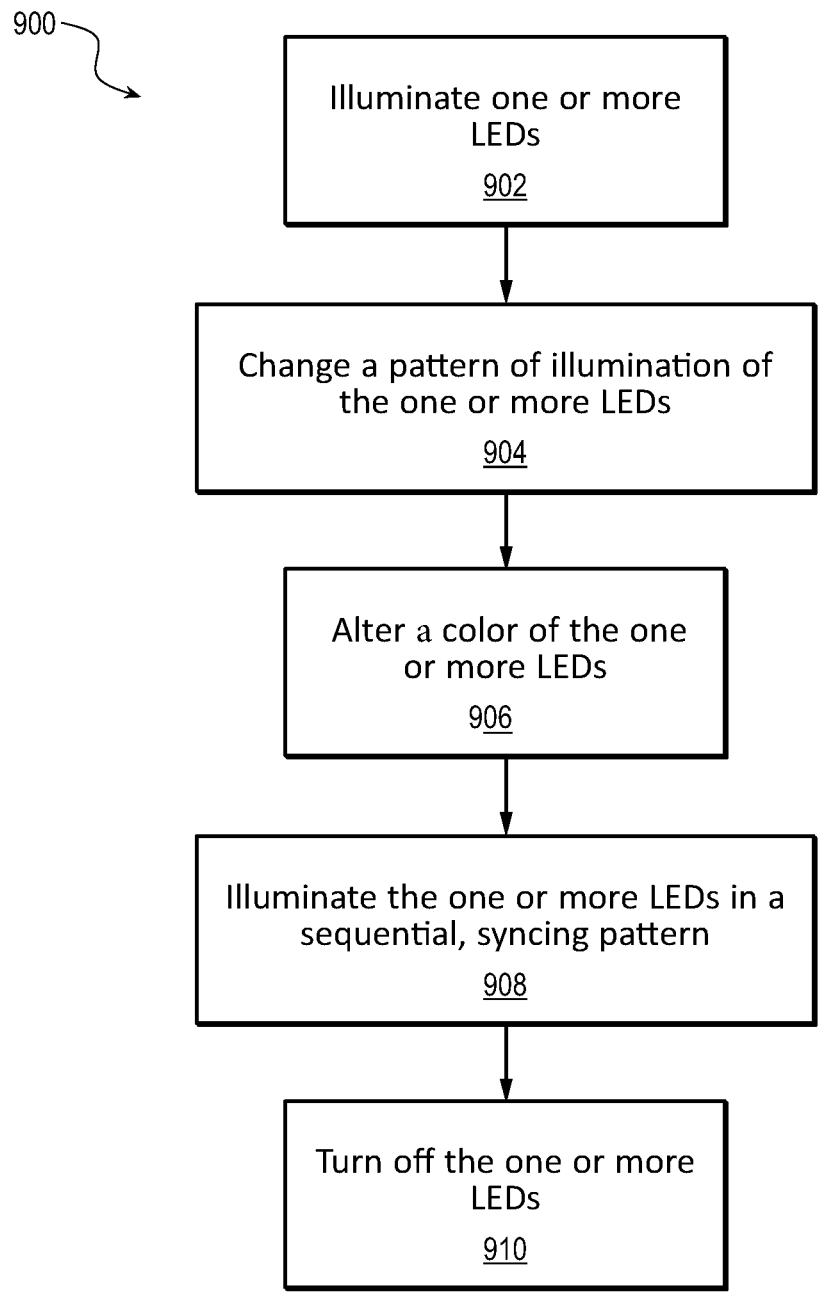
FIG. 9 is a flow diagram in accordance with exemplary embodiments described herein.

FIG. 9 is a flow chart illustrating an example of a method 900 for WCD systems, in accordance with various aspects of the present disclosure. For clarity, the method 900 is described below with reference to aspects of one or more of the systems described herein.

At block 902, the method 900 may illuminate one or more LEDs. For example, the method 900 may be issuing a status of the WCD, an alert, a positive feedback loop, or the like. The system may have one or multiple LEDs and may utilize specific LEDs for specific types of alerts or may utilize the LEDs in conjunction with each to issue alerts or notifications.

At block 904, the method 900 may change a pattern of illumination of the one or more LEDs. For example, the system status may have changed from a blinking green indicating a healthy system to a health alert or a system alert requiring attention. The method 900 may change the pattern of illumination to reflect the status changes. This may include changing the light from a solid light to a blinking, pulsing, flashing, or some combination thereof. In some embodiments, the method 900 may also change an intensity of the light based on the alert or ambient conditions. For example, the LEDs may have a high and low strength level that may change. Changing the luminous intensity may be a result of ambient lighting conditions or alert levels. For example, a system alert may indicate a high LED strength level, but a resolution may indicate a low strength level. Similarly, adjusting the luminous level for ambient lighting may make the WCD unit less intrusive to the patient.

At block 906, the method 900 may additionally or alternatively alter a color of the one or more LEDs. For example, the LEDs may be illuminated a first color which the method may change to a second color based at least in part on a system event, a physiological event, or the like. In some embodiments, the method 900 may change multiple LEDs if at least two LEDs are present in the system. The combination of different colors may communicate various statuses with the patient. For example, in some embodiments, one LED may communicate physiological condition while a second LED may communicate system conditions or status. If a physiological condition is detected that LED may turn from green to red, but the second LED may maintain a green status letting the patient and any potential bystanders know that the WCD is functioning properly.

At block 908, the method 900 may additionally or alternatively illuminate the one or more LEDs in a sequential syncing pattern. For example, two or more LEDs may blink sequentially. This may indicate a certain system status to the patient. The LEDs may also flash coincidentally or have a syncing color pattern of flashes, blinks, or pulses. The various illumination patterns may enable the method 900 to communicate with a user of the WCD.

At block 910, in some embodiments, the method 900 may turn off or deactivate one or more LEDs. For example, in some embodiments, all LEDs may be deactivated. In other embodiments, only specific LEDs may be active. The ability of the method to manipulate the patterns, colors, illumination, and brightness of the LEDs enable the method 900 to be less intrusive to patients while still enabling communication with the patient.

Thus, the method 900 may provide for one method of utilizing one or more LEDs in a WCD system. It should be noted that the method 900 is just one implementation and that the operations of the method 900 may be rearranged or otherwise modified such that other implementations are possible.

Figure 10:
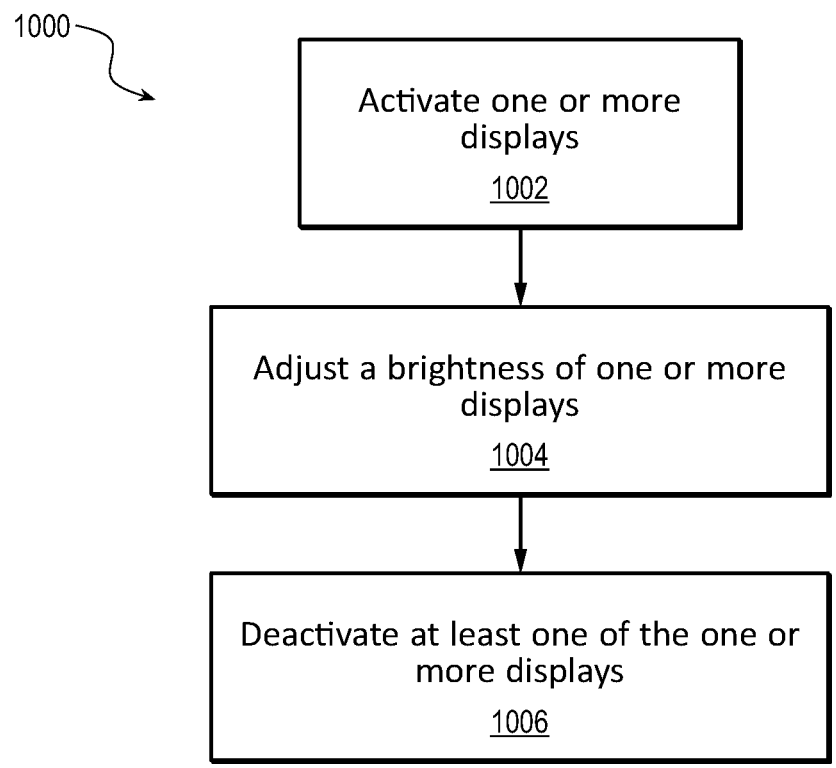
FIG. 10 is a flow diagram in accordance with exemplary embodiments described herein.

FIG. 10 is a flow chart illustrating an example of a method 1000 for WCD systems, in accordance with various aspects of the present disclosure. For clarity, the method 1000 is described below with reference to aspects of one or more of the systems described herein.

At block 1002, the method 1000 may include activating one or more displays proximate the WCD system based at least in part on an illumination threshold. The one or more displays may comprise a passive, reflective LCD display. In some embodiments, the illumination threshold may include at least one of an operational status, a patient status, a system status, an environmental status, an alarm status, and some combination thereof.

In some embodiments, the method 1000 may detect a system irregularity in the WCD. The method 1000 may detect a patient physiological condition. In some instances, the method may detect the amount of ambient lighting around the patient and WCD. In another embodiment, the method 1000 may detect user input to the WCD. In further embodiments, the method 1000 may detect a time of day or orientation of the device. In some embodiments, the method 1000 may determine a length of inactivity at the WCD or a length of time the display has been activated. The method 1000 may also detect a force acting on the display or an audible alert.

At block 1004, the method 1000 may adjust a brightness of the one or more displays. For example, depending on illumination threshold, the method 1000 may either increase the brightness of the display or lower the brightness of the display. In some embodiments, the method 1000 may put the display in standby mode. For example, at block 1006, the method may deactivate at least one of the one or more displays.

Thus, the method 1000 may provide for one method of manipulating one or more display screens in a WCD system. It should be noted that the method 1000 is just one implementation and that the operations of the method 900 may be rearranged or otherwise modified such that other implementations are possible.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method to alert a user of a wearable cardioverter defibrillator (WCD), the method comprising:
   detecting an abnormality in the WCD, wherein the abnormality includes at least one of a battery issue, an electrocardiogram (ECG) connectivity issue, an electrode connectivity issue, an electrode lead being disengaged from the WCD, or a connectivity issue;
   issuing a system alert based at least in part on the detection of the abnormality, wherein the system alert changes a brightness of a display from a first level to a second level;
   monitoring a status of the abnormality;
   determining that the status of the abnormality is resolved; and
   issuing an alert responsive to the determination that the status of the abnormality is resolved, wherein the alert changes the brightness of the display from the second level to the first level.

2. The method of claim 1 further comprising determining a severity rating for the abnormality.

3. The method of claim 2, further comprising:
   determining if the abnormality satisfies a time duration threshold based at least in part on the severity rating, wherein the issuing the system alert is further based on the abnormality satisfying the time duration threshold.

4. The method of claim 1, wherein the system alert further includes at least one of emitting a tone, changing display content, illuminating at least one LED, or emitting a vibration pattern.

5. The method of claim 1, wherein the user can customize the alert.

6. The method of claim 1, wherein issuing the alert further includes:
   activating a voice alert after a predetermined time threshold has been satisfied.

7. The method of claim 1, wherein the alert is issued for a predetermined time frame.

8. The method of claim 1, wherein the first level is a brightness of the display when the display is in a standby mode.

9. A wearable cardioverter defibrillator (WCD) system for monitoring health of a patient wearing the WCD system, the WCD system comprising:
   a support structure configured to be worn by the patient;
   electrocardiogram (ECG) electrodes coupled to the support structure;
   defibrillator electrodes configured to be proximate to the patient when the patient is wearing the WCD; and
   a processor communicatively coupled to the ECG electrodes,
   wherein the processor is configured to:
   detect an abnormality in the WCD, wherein the abnormality includes at least one of a battery anomaly, a loss of connectivity of the ECG electrodes, a loss of connectivity of the defibrillator electrodes, or a connectivity issue between the processor and an external device;
   issue a system alert based, at least in part, on detection of the abnormality, wherein the system alert changes a brightness of a display from a first level to a second level;
   monitor a status of the abnormality;
   determine that the status of the abnormality is resolved; and issue an alert responsive to the determination that the status of the abnormality is resolved, wherein the alert changes the brightness of the display from the second level to the first level.

10. The WCD system of claim 9, wherein the processor is further configured to:
determine a severity rating for the abnormality.

11. The WCD system of claim 10, wherein the processor is further configured to:
determine if the abnormality exceeds a time duration threshold based, at least in part, on the severity rating, and
issue the system alert based on the abnormality satisfying the time duration threshold.

12. The WCD system of claim 9, wherein the system alert further includes at least one of emitting a tone, changing display content, illuminating at least one LED, or emitting a vibration pattern.

13. The WCD system of claim 12, wherein the alert is configured to be customized by the patient.

14. The WCD system of claim 9, wherein the alert that is issued includes
activating a voice alert after a predetermined time threshold has been satisfied.

15. The WCD system of claim 9, wherein the alert is issued for a predetermined time frame.

16. The WCD system of claim 9, wherein the first level is a brightness of the display when the display is in a standby mode.

17. A method to alert a user of a wearable cardioverter defibrillator (WCD), the method comprising:
detecting an abnormality in the WCD, wherein the abnormality includes at least one of a battery issue, an electrocardiogram (ECG) connectivity issue, an electrode connectivity issue, a lead being disengaged from the WCD, or a connectivity issue;
issuing a system alert responsive at least in part to the detection of the abnormality, wherein the system alert changes a brightness of a display from a first level to a second level;
monitoring a status of the abnormality;
determining that the status of the abnormality is resolved; and
issuing an alert responsive to the determination that the status of the abnormality is resolved, wherein the alert changes the brightness of the display from the second level to the first level.

18. The method of claim 17 further comprising determining a severity rating for the abnormality.

19. The method of claim 18 further comprising determining if the abnormality satisfies a time duration threshold based at least in part on the severity rating, wherein the issuing the system alert is further based on the abnormality satisfying the time duration threshold.

* * * * *